US010565707B2

(12) United States Patent
Liu et al.

(10) Patent No.: US 10,565,707 B2
(45) Date of Patent: Feb. 18, 2020

(54) 3D ANISOTROPIC HYBRID NETWORK: TRANSFERRING CONVOLUTIONAL FEATURES FROM 2D IMAGES TO 3D ANISOTROPIC VOLUMES

(71) Applicant: Siemens Healthcare GmbH, Erlangen (DE)

(72) Inventors: Siqi Liu, Princeton, NJ (US); Daguang Xu, Princeton, NJ (US); Shaohua Kevin Zhou, Plainsboro, NJ (US); Thomas Mertelmeier, Erlangen (DE); Julia Wicklein, Neunkirchen a. Br. (DE); Anna Jerebko, Paoli, PA (US); Sasa Grbic, Plainsboro, NJ (US); Olivier Pauly, Munich (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 136 days.

(21) Appl. No.: 15/996,719

(22) Filed: Jun. 4, 2018

(65) Prior Publication Data

US 2019/0130562 A1 May 2, 2019

Related U.S. Application Data

(60) Provisional application No. 62/580,477, filed on Nov. 2, 2017.

(51) Int. Cl.
*G06K 9/00* (2006.01)
*G06T 7/00* (2017.01)
(Continued)

(52) U.S. Cl.
CPC ........ *G06T 7/0012* (2013.01); *G06K 9/00201* (2013.01); *G06K 9/4628* (2013.01);
(Continued)

(58) Field of Classification Search
CPC . G06T 7/0012; G06T 7/11; G06T 7/62; G06T 11/60; G06T 11/008; G06T 15/00;
(Continued)

(56) References Cited

U.S. PATENT DOCUMENTS 9,589,374 B1 * 3/2017 Gao ...................... G06T 11/008
9,968,257 B1 * 5/2018 Burt ...................... A61B 5/7267
(Continued)

OTHER PUBLICATIONS

Jia, Haozhe et al., "3D Global Convolutional Adversarial Network for Prostate MR Volume Segmentation", arXiv:1807.06742v1 [cs.CV] Jul. 18, 2018, pp. 1-9. (Year: 2018).*
(Continued)

*Primary Examiner* — Jose L Couso (57) ABSTRACT

A computer-implemented method for identifying features in 3D image volumes includes dividing a 3D volume into a plurality of 2D slices and applying a pre-trained 2D multi-channel global convolutional network (MC-GCN) to the plurality of 2D slices until convergence. Following convergence of the 2D MC-GCN, a plurality of parameters are extracted from a first feature encoder network in the 2D MC-GCN. The plurality of parameters are transferred to a second feature encoder network in a 3D Anisotropic Hybrid Network (AH-Net). The 3D AH-Net is applied to the 3D volume to yield a probability map;. Then, using the probability map, one or more of (a) coordinates of the objects with non-maximum suppression or (b) a label map of objects of interest in the 3D volume are generated.

17 Claims, 9 Drawing Sheets
(3 of 9 Drawing Sheet(s) Filed in Color)

(51) Int. Cl.

| | |
|---|---|
| *G06K 9/62* | (2006.01) |
| *G06T 11/60* | (2006.01) |
| *G06N 3/04* | (2006.01) |
| *G16H 30/20* | (2018.01) |
| *G06K 9/46* | (2006.01) |

(52) U.S. Cl.
CPC ......... *G06K 9/6232* (2013.01); *G06K 9/6273* (2013.01); *G06K 9/6277* (2013.01); *G06N 3/04* (2013.01); *G06T 11/60* (2013.01); *G16H 30/20* (2018.01); *G06T 2207/10112* (2013.01); *G06T 2207/20081* (2013.01); *G06T 2207/20084* (2013.01); *G06T 2207/30068* (2013.01)

(58) Field of Classification Search
CPC ......... G06T 15/08; G06T 17/00; G06T 17/10; G06T 19/00; G06T 2200/04; G06T 2200/08; G06T 2207/10112; G06T 2207/20081; G06T 2207/20084; G06T 2207/30068; G06T 2207/30096; G06T 2207/30056; G06T 2207/30004; G06T 2207/30048; G06T 2207/30061; G06T 2207/30084; G06T 2207/30092; G06T 2207/30064; G06T 2207/10081; G06T 2207/10072; G06T 2207/70088; G06T 2207/20101; G06T 2207/30016; G06T 2210/41; G06T 2219/00; G06K 9/00201; G06K 9/4628; G06K 9/6232; G06K 9/6273; G06K 9/6277; G06K 9/3241; G06K 9/6261; G06K 9/46; G06K 9/00523; G06K 2209/05; G06K 2209/053; G06K 2209/40; G06N 3/04; G06N 3/02; G06N 3/0454; G06N 3/08; G06N 3/084; G16H 30/20; G16H 30/40; G16H 50/20; A61B 2576/00; A61B 2576/023; A61B 5/7267; A61B 5/7485; A61B 5/055; A61B 5/0035; A61B 5/0044; A61B 6/466; A61B 8/466; A61B 8/469; A61B 8/483; G01R 33/4835
See application file for complete search history.

(56) References Cited

U.S. PATENT DOCUMENTS

| | | | | |
|---|---|---|---|---|
| 2018/0240235 | A1* | 8/2018 | Mazo | G16H 50/50 |
| 2018/0259608 | A1* | 9/2018 | Golden | G06N 3/084 |
| 2018/0365825 | A1* | 12/2018 | Salafia | G06T 7/0012 |

OTHER PUBLICATIONS

American Cancer Society. Cancer Facts and Figures 2017. American Cancer Society, 2017.
T. Brosch, L. Y.W. Tang, Y. Yoo, D. K. B. Li, A. Traboulsee, and R. Tam. Deep 3D Convolutional Encoder Networks With Shortcuts for Multiscale Feature Integration Applied to Multiple Sclerosis Lesion Segmentation. IEEE Transactions on Medical Imaging, 35(5):1229-1239, May 2016.
Chaurasia, Abhishek, and Eugenio Culurciello. "LinkNet: Exploiting Encoder Representations for Efficient Semantic Segmentation." arXiv preprint arXiv:1707.03718 (2017).
J. Chen, L. Yang, Y. Zhang, M. Alber, and D. Z. Chen. Combining Fully Convolutional and Recurrent Neural Networks for 3D Biomedical Image Segmentation, 2016.
Cicek, A. Abdulkadir, S. S. Lienkamp, T. Brox, and O. Ronneberger. 3D U-Net: Learning Dense Volumetric Segmentation from Sparse Annotation. Jun. 2016.
F. C. Ghesu, B. Georgescu, S. Grbic, A. K. Maier, J. Hornegger, and D. Comaniciu. Robust Multi-scale Anatomical Landmark Detection in Incomplete 3D-CT Data. pp. 194-202. Springer, Cham, Sep. 2017.
K. He, X. Zhang, S. Ren, and J. Sun. Deep residual learning for image recognition. Proceedings of the IEEE, 2016.
G. Huang, Z. Liu, K. Q. Weinberger, and L. van derMaaten, "Densely connected convolutional networks",in Computer Vision and Pattern Recognition (CVPR), 2017.
Ioffe, Sergey, and Christian Szegedy. "Batch normalization: Accelerating deep network training by reducing internal covariate shift." arXiv preprint arXiv:1502.03167 (2015).
Kingma Diederik P et al: "Adam: A method for stochastic optimization" ICLR 2015, retrieved from the Internet: URL:https://arxiv.org/pdf/1412.6980v8.pdf.
Lee, K., Zung, J., Li, P., Jain, V., & Seung, H. S. (2017). Superhuman accuracy on the SNEMI3D connectomics challenge. arXiv preprint arXiv:1706.00120.
Li, X., Chen, H., Qi, X., Dou, Q., Fu, C. W., & Heng, P. A. (2017). H-DenseUNet: Hybrid densely connected UNet for liver and liver tumor segmentation from CT volumes. arXiv preprint arXiv:1709.07330.
Lin, T. Y., Goyal, P., Girshick, R., He, K., & Dollár, P. (2017). Focal loss for dense object detection. arXiv preprint arXiv:1708.02002.
Liu, F., Zhou, Z., Jang, H., Samsonov, A., Zhao, G., & Kijowski, R. (2018). Deep convolutional neural network and 3D deformable approach for tissue segmentation in musculoskeletal magnetic resonance imaging. Magnetic resonance in medicine, 79(4), 2379-2391.
P. Moeskops, M. A. Viergever, A. M. Mendrik, L. S. de Vries, M. J. N. L. Benders, and I. Isgum. Automatic Segmentation of MR Brain Images With a Convolutional Neural Network. IEEE Transactions on Medical Imaging, 35(5):1252-1261, May 2016.
Peng, Chao, et al. "Large Kernel Matters—Improve Semantic Segmentation by Global Convolutional Network." arXiv preprint arXiv:1703.02719 (2017).
Qiu, Zhaofan, Ting Yao, and Tao Mei. "Learning spatio-temporal representation with pseudo-3d residual networks." 2017 IEEE International Conference on Computer Vision (ICCV). IEEE, 2017.
S. Ren, K. He, R. Girshick, and J. Sun. Faster R-CNN: Towards Real-Time Object Detection with Region Proposal Networks, 2015.
Russakovsky, Olga, et al. "Imagenet large scale visual recognition challenge." International Journal of Computer Vision 115.3 (2015): 211-252.
Russakovsky, Olga, Jia Deng, Hao Su, Jonathan Krause, Sanjeev Satheesh, Sean Ma, Zhiheng Huang et al. "Imagenet large scale visual recognition challenge." International Journal of Computer Vision 115, No. 3 (2015):211-252.
Wang, Guotai, et al. "Automatic brain tumor segmentation using cascaded anisotropic convolutional neural networks." arXiv preprint arXiv:1709.00382 (2017).
Zeng, Tao, Bian Wu, and Shuiwang Ji. "DeepEM3D: approaching human-level performance on 3D anisotropic EM image segmentation." Bioinformatics 33.16 (2017): 2555-2562.
Zhao, Hengshuang, et al. "Pyramid scene parsing network." IEEE Conf. on Computer Vision and Pattern Recognition (CVPR). 2017.
Extended European Search Report (EESR) dated Feb. 26, 2019 in corresponding European Patent Application No. 18203241.7.
Liu, Siqi, et al., "3D anisotropic hybrid netword: transferring convolutional features form 2D images to 3D anisotropic volumes", Dec. 14, 2017, arxiv.org/pdf/1711.08580.pdf.
Ronneberger, Olaf et al. "U-Net: Convolutional Networks for Biomedical Image Segmentation" ; May 18, 2015; Medical Image Computing and Computer-Assisted Intervention (MICCAI), Springer, LNCS, vol. 9351, pp. 234-241.

\* cited by examiner

| Original Image with ground truth lesion centers | Overlaid output of 2D network Multi-channel GCN | Overlaid output of 3D AH-Net |
|---|---|---|
|  |  |  |
|  |  |  |

# 3D ANISOTROPIC HYBRID NETWORK: TRANSFERRING CONVOLUTIONAL FEATURES FROM 2D IMAGES TO 3D ANISOTROPIC VOLUMES

CROSS-REFERENCE TO RELATED APPLICATIONS

This application is related to, and claims benefit to and priority of, U.S. Patent Application Ser. No. 62/580,477, filed on Nov. 2, 2017, the contents of which are hereby incorporated by reference in their entirety for all purposes.

TECHNOLOGY FIELD

The present invention relates generally to methods, systems, and apparatuses related to a 3D anisotropic hybrid network for transferring convolutional features from 2D images to 3D anisotropic volumes. The disclosed methods, systems, and apparatuses may be applied to, for example, breast lesion detection from DBT image volumes, and liver tumor segmentation applications.

BACKGROUND 3D volumetric images (or "volumes") are widely used for clinical diagnosis, surgical planning and biomedical research. The 3D context information provided by such volumetric images is important for visualizing and analyzing the object of interest. However, given the added dimension, it is more time consuming and sometimes harder to interpret 3D volumes than 2D images by machines. Many conventional systems use convolutional neural networks (CNN) to extract the representation of structural patterns of interests in human or animal body tissues.

Due to the special imaging settings, many imaging modalities come with anisotropic voxels, meaning not all the three dimensions have equal resolutions. For example, in the 3D volumes of Digital Breast Tomosynthesis (DBT), and sometimes Computed Tomography (CT), the image resolution in xy plane/slice (or within-slice resolution) is more than ten times higher than that of the z resolution (or between-slice resolution). Thus, the xy slices preserve much more information than the z dimension. In DBT images, only the spatial information within the xy plane can be guaranteed. However, the 3D context between xy slices, even with slight misalignment, still carries meaningful information for analysis. Directly applying 3D CNN to such images remains a challenging task due to the following reasons. First, it may be hard for a small 3×3×3 kernel to learn useful features from anisotropic voxels, because of the different information density along each dimension. Second, theoretically more features are needed in 3D networks compared to 2D networks. The capability of 3D networks is bounded by the GPU memory, constraining both the width and depth of the networks. Third, unlike 2D computer vision tasks which nowadays can make use of the backbone networks pre-trained using millions of 2D images, 3D tasks mostly have to train from scratch, and hence suffer from the lack of large 3D datasets. In addition, the high data variations make the 3D networks harder to be trained. Also, 3D CNNs trained on such small image datasets with relatively small context are hard to generalize to unseen data.

Besides the traditional 3D networks built with 1×1×1 and 3×3×3 kernels, there are other conventional methods for learning representations from anisotropic voxels. Some methods process 2D slices separately with 2D networks. To make a better use of the 3D context, more than one image slice is used as the input for 2D networks. The 2D slices can also be viewed sequentially by combining a fully convolutional network (FCN) architecture with Convolutional LSTM to view the adjacent image slices as a time series to distil the 3D context from a sequence of abstracted 2D context. There are also conventional methods that apply anisotropic convolutional kernels to distribute more learning capability on the xy plane than on the z axis.

SUMMARY

The present invention, as described in various embodiments herein, describes a 3D anisotropic hybrid network (AHNet) for transferring convolutional features from 2D images to a 3D network for deep learning applications with 3D anisotropic volumes. Such a transfer inherits the desired strong generalization capability for within slice information while naturally exploiting between-slice information for more effective modelling. The focal loss is further utilized for more effective end-to-end learning. The technology described herein, may be applied to medical image analysis tasks, such as lesion detection from a Digital Breast Tomosynthesis volume, and liver tumor segmentation from a Computed Tomography volume.

According to some embodiments of the present invention, a computer-implemented method for identifying features in 3D image volumes includes dividing a 3D volume into 2D slices and applying a pre-trained 2D multi-channel global convolutional network (MC-GCN) to the 2D slices until convergence. Following convergence of the 2D MC-GCN, parameters are extracted from a first feature encoder network in the 2D MC-GCN. The parameters are transferred to a second feature encoder network in a 3D AH-Net. The 3D AH-Net is applied to the 3D volume to yield a probability map. Then, using the probability map, one or more of (a) coordinates of the objects with non-maximum suppression or (b) a label map of objects of interest in the 3D volume are generated.

According to other embodiments, a computer-implemented method for identifying features in 3D image volumes includes dividing a 3D digital breast tomosynthesis (DBT) volume into 2D slices and applying a 2D MC-GCN to the 2D slices until convergence, wherein the 2D MC-GCN is pre-trained with DBT image slices depicting healthy breast tissue. Following convergence of the 2D MC-GCN, parameters are extracted from a first feature encoder network in the 2D MC-GCN and transferred to a second feature encoder network in a 3D AH-Net. The 3D AH-Net is applied to the 3D volume to yield a voxel-wise confidence map of lesion presence comprising a confidence score for each voxel in the 3D volume indicating presence or absence of a lesion. Then, the voxel-wise confidence map is presented overlaid on the 3D DBT volume.

In other embodiments of the present invention, a system for identifying features in 3D image volumes includes a 2D MC-GCN, a 3D AH-Net, and a parallel processing architecture. The 2D MC-GCN comprises a 2D feature encoder network, while the 3D AH-Net comprises a 3D feature encoder network. The 3D AH-Net further comprises decoder modules configured to process outputs of the 3D feature encoder, a pyramid volumetric pooling module configured to process outputs of the decoder modules to generate a probability map pyramid, and a concatenation module configured to concatenate the probability map pyramid and outputs of the decoder modules to generate a probability map. The parallel processing architecture is configured to divide a 3D volume into 2D slices and apply the 2D MC-GCN to the 2D slices until convergence. Following convergence of the 2D MC-GCN, the parallel processing architecture extracts parameters from a 2D feature encoder network in the 2D MC-GCN and transfers the parameters to the 3D feature encoder network in the 3D AH-Net. The parallel processing architecture then applies the 3D AH-Net to the 3D volume to generate a probability map.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed.

The patent or application file contains at least one drawing executed in color. Copies of this patent or patent application publication with color drawing(s) will be provided by the Office upon request and payment of the necessary fee.

Included in the drawings are the following Figures.

DETAILED DESCRIPTION OF ILLUSTRATIVE EMBODIMENTS

The following disclosure describes the present invention according to several embodiments directed at methods, systems, and apparatuses related to a 3D anisotropic hybrid network for transferring convolutional features from 2D images to 3D anisotropic volumes. More specifically, the techniques described herein disclose a 3D Anisotropic Hybrid Network (AH-Net) to learn informative features from images with anisotropic resolution. To obtain the 3D AH-Net, first a 2D fully convolutional ResNet is trained. The 2D network may be initialized with pre-trained weights and uses multiple 2D image slices as inputs. The feature encoder of the 2D network is then transformed into a 3D network by extending the 2D kernel with one added dimension. Then a feature decoder sub-network is added to extract the 3D context. The feature decoder sub-network comprises anisotropic convolutional blocks with 3×3×1 and 1×1×3 convolutions. Different anisotropic convolutional blocks are combined with dense connections. Connections between the feature encoder and the decoder are skipped. A pyramid volumetric pooling module is stacked at the end of the network before the final output layer for extracting multi-scale features. Because AH-Net can make use of 2D networks pre-trained with large 2D general image datasets such as ImageNet, it is easier to train as well as to generalize. The anisotropic convolutional blocks enable it to exploit the 3D context. With end-to-end inference as a 3D network, AH-Net runs much faster than the conventional multi-channel 2D networks regarding the GPU time required for processing each 3D volume.

The AH-Net comprises a feature encoder and a feature decoder. The encoder, transformed from a 2D network, is designed for extracting the deep representations from 2D slices with high resolution. The decoder, built with densely connected blocks of anisotropic convolutions, is responsible for exploiting the 3D context and maintaining the between-slice consistency. The network training is performed in two stages: the encoder is learned; then the 3D decoder is added and fine-tuned with the encoder parameters locked. To perform end-to-end hard voxel mining, the Focal Loss (FL) is used in some embodiments. As is generally known in the art FL was originally designed for object detection.

Learning a Multichannel 2D Feature Encoder

Figure 1:
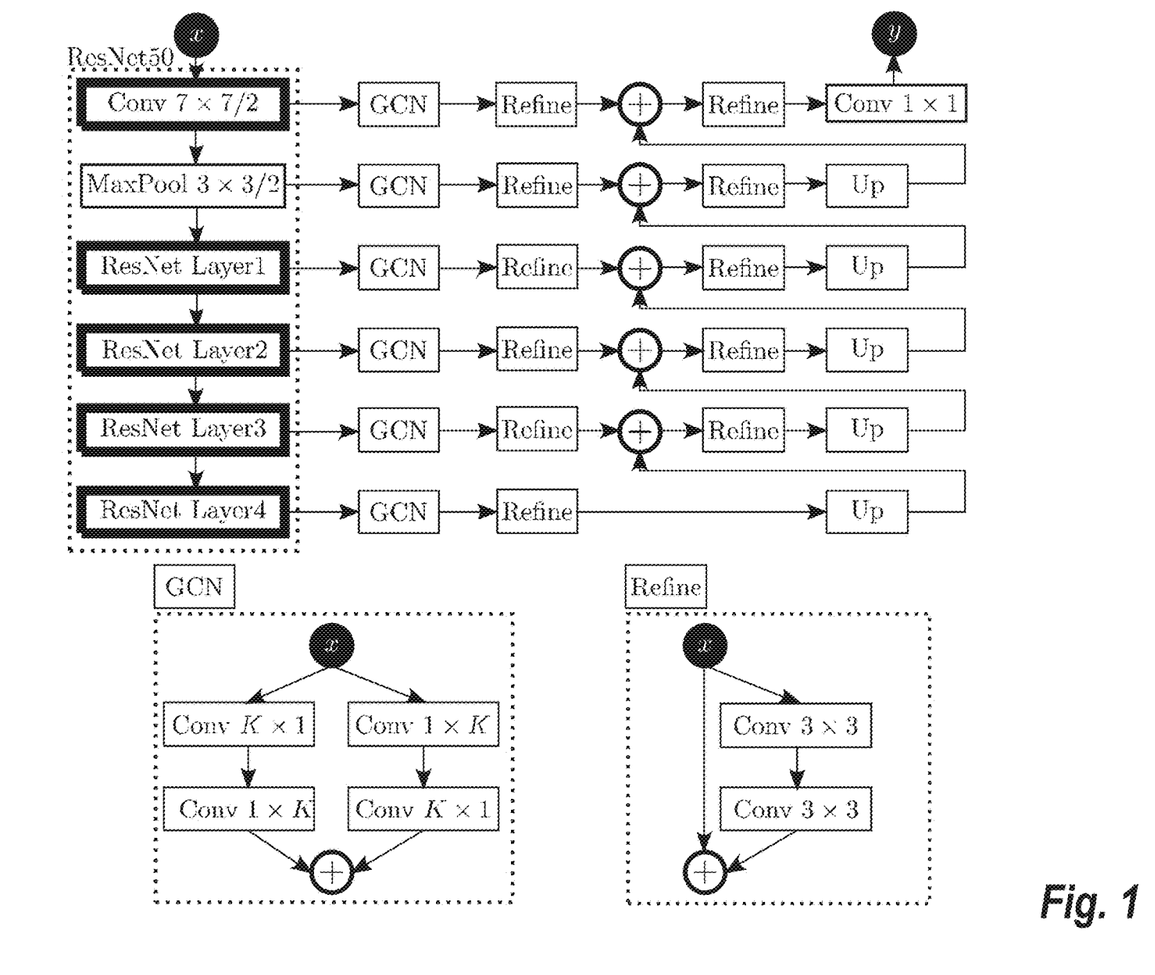
FIG. 1 illustrates the network architecture for pre-training the 2D encoder network Multi-Channel Global Convolutional Neural Network (MC-GCN)

FIG. 1 illustrates the network architecture for pre-training the 2D encoder network Multi-Channel Global Convolutional Neural Network (MC-GCN). The ResNet50 is used as the back-bone network, initialized with ImageNet images. The global convolutional network modules and refinement modules are added to the encoder network to increase the receptive field during the pre-training as well as to increase the output response map to the original resolution. Conv K×K/S represents a convolution layer with the kernel size K and the stride size S in each dimension. The upsampling module (Up) comprises a Conv 1×1 projection layer and a bi-linear upsampling layer.

In the example of FIG. 1, a 2D multi-channel global convolutional network (MC-GCN) is trained to extract the 2D within-slice features at different resolutions. In some embodiments, the ResNet50 model is used as the back-bone network which is initialized by pre-training with the ImageNet images, although other pre-trained networks would work similarly. The network is then fine-tuned with 2D image slices extracted from the 3D volumes. The input to this network is three neighboring slices (treated as RGB channels). Thus, the entire architecture of the ResNet50 remains unchanged.

The multi-channel 2D input could enable the 2D network to fuse the between-slice context at an early stage. A decoder is added to accompany the encoder to upscale the response map to the original resolution. The examples described herein employ a decoder architecture with the global convolutional networks (GCN) and refinement blocks; however it should be understood that similar architectures may be employed in different embodiments. The GCN module simulates a large K×K convolutional kernel by decomposing it into two 1-D kernels (1×K and K×1). Two branches containing the 1D kernels permuted in different orders are merged by summation. The output of each GCN module contains the same number of output maps as the final outputs. The large kernels simulated by GCNs ensure that the network has a large receptive field at each feature resolution. Each refinement block contains two 3×3 convolutions with a ReLU activation in the middle. The input of each refinement block is also added to its output to form a residual connection. At the end of each encoder resolution level, the features are fed into GCN modules with the kernel sizes of 63, 31, 15, 9, 7, and 5, respectively. The output features are fed into a refinement block and summed with the features upsampled from a lower resolution level. The summed features are fed into another refinement block and upsampled with a 1×1 convolution and a bi-linear upsampling layer. The final output has the same resolution as the image input. The decoder has only a small number of parameters with little computational cost. The light-weight decoder makes the encoder features easier to be transferred to the 3D AH-Net since the majority of the feature learning relies on the encoder network.

Transferring the Learned 2D Network to 3D AHNet

Figure 2:
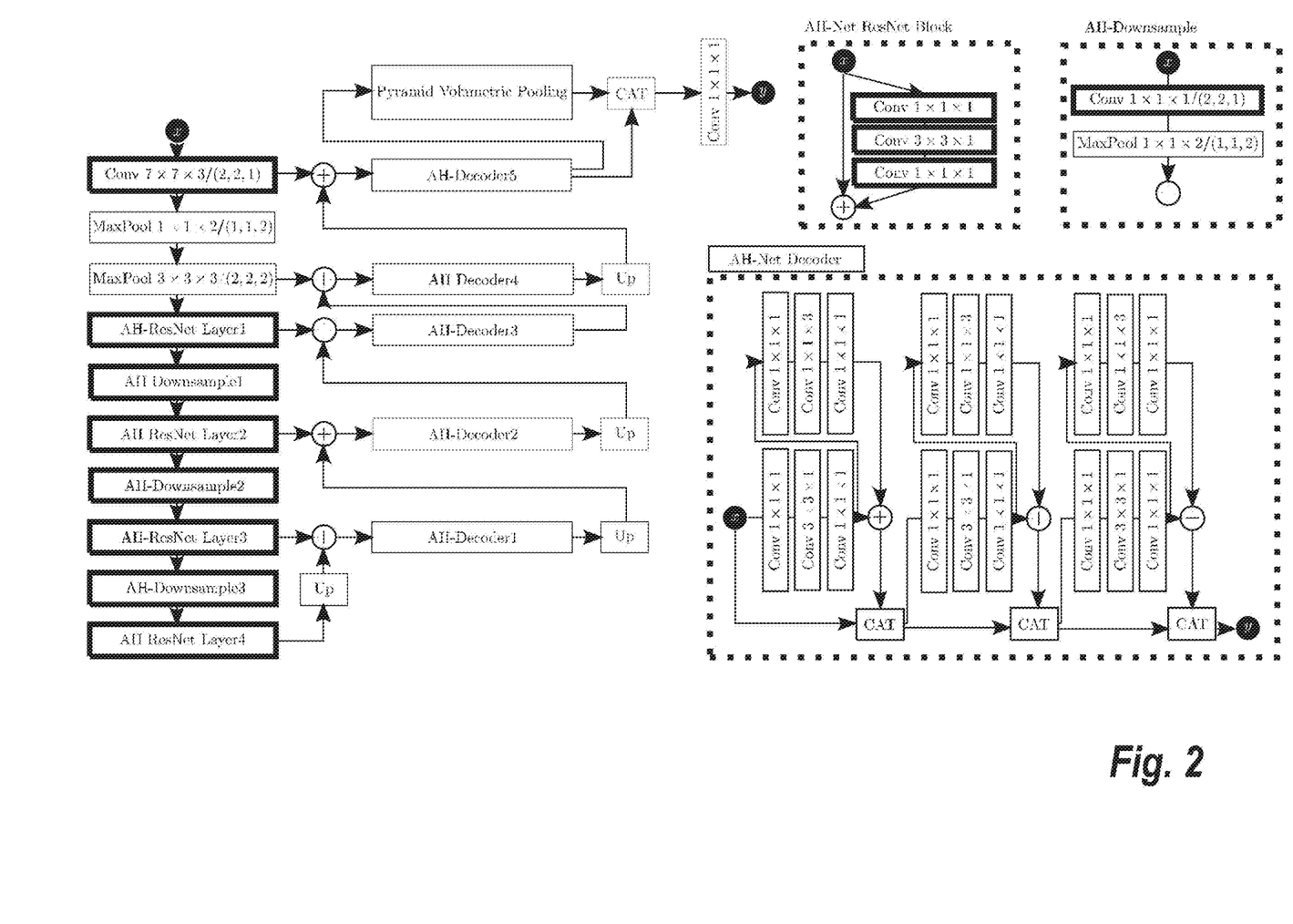
FIG. 2 shows an example architecture of 3D AH-Net, as it may be implemented in some embodiments.

FIG. 2 shows an example architecture of 3D AH-Net, as it may be implemented in some embodiments. The feature encoder with AH-ResNet blocks is transferred from the pre-trained 2D network with 1×1×1 and 3×3×1 convolutions. The features are then processed with the AH-Net decoders which are designed with 3×3×1 and 1×1×3 convolutional blocks. Feature summation may be used instead of concatenation to support more probability maps with less memory consumption. It should be noted that this example hides the batch normalization and ReLu layers for brevity. The weights of the blocks with thick black borders are transformed from the 2D MC-GCN.

After the 2D MC-GCN network converges, the parameters of its encoder are extracted and transferred to the corresponding encoder layers of AH-Net. The decoder part of the 2D MC-GCN is discarded and instead a new decoder for the AH-Net is employed that comprises multiple levels of densely connected blocks, followed by a pyramid volumetric pooling module for extracting the multiscale feature responses. The parameters of the new decoder are randomly initialized. The input and output of AH-Net are now 3D patches, similar to other conventional 3D CNN.

Figure 3:
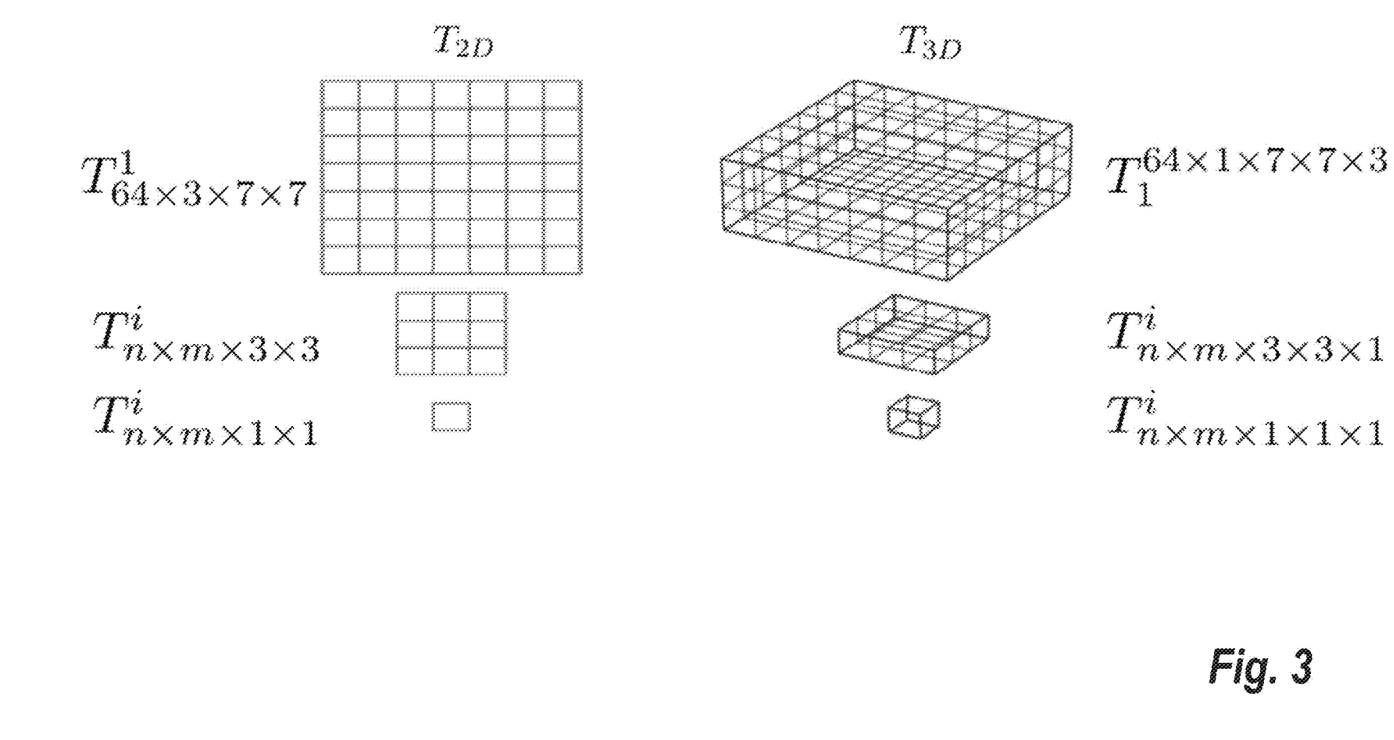
FIG. 3 illustrates transforming the 2D convolutional weight tensor.

The transformation of convolution tensors from 2D to 3D is illustrated in FIG. 3, which aims to perform 2D convolutions on 3D volumes slice by slice in the encoder part of AH-Net. More specifically, FIG. 3 illustrates transforming the 2D convolutional weight tensor $T_{2D}$ to 3D $T_{3D}$, where m and n are the number of features and channels of a layer, respectively. The first layer weight tensor $T_{64\times 3\times 7\times 7}^{1}$ is transformed to $T_{64\times 1\times 7\times 7\times 3}^{1}$. The other convolutional kernels may be transformed by adding an extra dimension.

Notation

In the present disclosure, a 2D convolutional tensor is denoted by $T_{n\times m\times h\times w}^{i}$ where n, m, h, and w, respectively, represent the number of output channels, the number of input channels, the height and width of the $i^{th}$ convolution layer. Similarly, a 3D weight tensor is denoted by $T_{n\times m\times h\times w\times d}^{i}$ where d is the filter depth. $P^{(b,a,c,d)}(T_{a\times b\times c\times d})$ denotes the dimension permutation of a tensor $T_{a\times b\times c\times d}$, resulting in a new tensor $T_{b\times a\times c\times d}$ with the 1st and 2nd dimensions switched. $P^{(a,*,b,c,d)}(T_{a\times b\times c\times d})$ adds an identity dimension between the 1st and 2nd dimensions of the tensor $T_{a\times b\times c\times d}$ and gives $(T_{a\times 1\times b\times c\times d})$. A convolutional layer is defined as Conb $K_x \times K_y \times K_z/(S_x,S_y,S_z)$, where $K_x$, $K_y$, $K_z$ are the kernel sizes; $S_x$, $S_y$, $S_z$ are the stride side in each direction. Max pooling layers are denoted by MaxPool $K_x \times K_y \times K_z/(S_x, S_y, S_z)$. The stride is omitted when a layer has a stride size of 1 in all dimensions.

Input Layer Transform

The input layer of the 2D MC-GCN contains a convolutional weight tensor $T_{64\times 3\times 7\times 7}^{1}$ inherited from its ResNet50 back-bone network. The 2D convolutional tensor $T_{64\times 3\times 7\times 7}^{1}$ is transformed as:

$$P^{(1,*,3,4,2)}(T_{64\times 3\times 7\times 7}^{1})=T_{64\times 1\times 7\times 7\times 3}^{1} \quad (1)$$

in order to form a 3D convolution kernel that convolves 3 neighboring slices. To keep the output consistent with the 2D network, in some embodiments, only the stride-2 convolutions are applied on the xy plane and stride 1 on the third dimension. This results in the input layer Conv 7×7×3/(2, 2,1). To downsample the z dimension, a MaxPool 1×1×2/ (1,1,2) may be applied to fuse every pair of the neighboring slices. An additional MaxPool 2×2×2/(2,2,2) is used to keep the feature resolution consistent with the 2D network.

ResNet Block Transform

All the 2D convolutional tensors $T_{n\times m\times 1\times 1}^{i}$ and $T_{n\times m\times 3\times 3}^{i}$ in the ResNet50 encoder are transformed as:

$$P^{(1,2,3,4,*)}(T_{n\times m\times 1\times 1}^{i})=T_{n\times m\times 1\times 1\times 1}^{i} \quad (2)$$

and $$P^{(1,2,3,4,*)}(T_{n\times m\times 3\times 3}^{i})=T_{n\times m\times 3\times 3\times 1}^{i} \quad (3)$$

In this way, all the ResNet Conv 3×3×1 blocks as shown in FIG. 3 only perform 2D slice-wise convolutions on the 3D volume within the xy plane. The original downsampling between ResNet blocks is performed with Conv 1×1/(2,2). However, in a 3D volume, a Conv 1×1×1/(2,2,2) skips a slice for every step on the z dimension. This would miss important information when the image only has a small number of slices along the z dimension, especially for detection tasks. To address this issue, a Conv 1×1×1/(2,2,1) is used, followed by a MaxPool 1×1×2/(1,1,2) to downsample the 3D probability maps between the ResNet blocks as shown in the AH-Downsample block in FIG. 2. This MaxPooling simply takes the maximum response along the z direction between 2 neighboring slices. This allows for the use of large and deep networks on 3D data with limited GPU memory.

Anisotropic Hybrid Decoder

Accompanying to the transformed encoder, an anisotropic 3D decoder sub-network is added to exploit the 3D anisotropic image context. In the decoder, anisotropic convolutional blocks with Conv 1×1×1, Conv 3×3×1 and Conv 1×1×3 are used. The features are passed into an xy bottleneck block at first with a Conv 3×3×1 surrounded by two layers of Conv 1×1×1. The output is then forwarded to another bottleneck block with a Conv 1×1×3 in the middle and summed with itself before forwarding to the next block. This anisotropic convolution block decomposes a 3D convolution into 2D and 1D convolutions. It receives the inputs from the pre previous layers using a 2D convolution at first, preserving the detailed 2D features. Conv 1×1×3 mainly fuses the within-slice features to keep the z dimension output consistent.

Three anisotropic convolutional blocks are connected as the densely connected neural network using feature concatenation for each resolution of encoded features. Similar to LinkNet, the features received from each resolution of the encoder are firstly projected to match the number of features of the higher encoder feature resolution using a Conv 1×1×1. They are then upsampled using the 3D tri-linear interpolation and summed with the encoder features from a higher resolution. The summed features are forwarded to the decoder blocks in the next resolution At the end of the decoder network, a pyramid volumetric pooling module is employed to obtain multi-scaled features. The output features of the last decoder block are firstly down-sampled using 4 different Maxpooling layers, namely MaxPool 64×64×1, MaxPool 32×32×1, MaxPool 16×16×1 and MaxPool 8×8×1 to obtain a probability map pyramid. Conv 1×1×1 layers are used to project each resolution in the feature pyramid to a single response channel. The response channels are then interpolated to the original size and concatenated with the features before downsampling. The final outputs are obtained by applying a Conv 1×1×1 projection layer on the concatenated features.

Training AHNet using Focal Loss

Training AH-Net using the same learning rate on both the pre-trained encoder and the randomly initialized decoder would make the network difficult to optimize. To train the 3D AH-Net, all the transferred parameters are locked at first. Only the decoder parameters are fine-tuned in the optimization. All the parameters can be then fine-tuned altogether afterwards to the entire AH-Net jointly. The training of 3D fully convolution networks tend to pre-mature on the easy voxels quickly and converge slowly on the hard voxels, which are sometimes the objects of interests in medical images. For example, FCNs would learn the background voxels with uniform distributions quickly. For small-scaled patterns, such as lesions and object boundaries, the numeric errors tend to be small in the averaged losses. It would thus make the training insensitive to the subtle differences between the network outputs and the ground truth maps. Focal Loss (FL), derived from the Focal Loss for object detection, is used to perform the hard-voxel-mining with the AH-Net.

To demonstrate the efficacy and efficiency of the proposed 3D AH-net, two examples are described in detail below: lesion detection from a Digital Breast Tomosynthesis (DBT) volume and liver tumor segmentation from a Computed Tomography (CT) volume. FL regarding the L2 loss is used in the DBT volume example described below. The cross-entropy form of FL employed in the CT volume example described below can be found in Lin, T., Goyal, P., Girshick, R. B., He, K., & Dollár, P. (2017). Focal Loss for Dense Object Detection. 2017 *IEEE International Conference on Computer Vision (ICCV)*, 2999-3007. Assuming the L2 loss $D(y, \hat{y})$ is used for supervised learning of a regression map, $$F_{FL}(y, \hat{y}) = \left(\frac{\ln D(y, \hat{y})}{\ln D_{max}(y, \hat{y})}\right)^{\gamma} D(y, \hat{y}) \qquad (4)$$

where $D_{max}(y, \hat{y})$ is the maximum numeric value expected for the L2 loss. The focusing parameter down-weights the easy voxels. A large value would make the training focus more on the large numeric errors generated on the hard-voxels. The original L2 loss is replaced with FL after a few epochs when the L2 loss barely decreases. The training loss could keep descending for more epochs under FL with the output details progressively enhanced.

Demonstrative Examples

In the examples described below, all the compared networks were optimized with $\beta1=0.9$, $\beta2=0.999$, and $\epsilon=10^{-8}$. This optimization may be performed, for example, using the techniques described in Kingma, D. P., & Ba, J. (2014). Adam: A Method for Stochastic Optimization. *CoRR, abs/1412.6980*. An initial learning-rate of 0.0005 is used to fine-tune the 2D Multi-Channel GCN. Then, the learning rate is increased to 0.001 to fine-tune the AH-Net after the 2D network is transferred. This is based on the empirical finding that 3D networks generally need a larger learning-rate to converge within a reasonable amount of time. Each of the networks described herein may be implemented using any deep learning framework know in the art (e.g., Pi-Torch).

For the first example described below, a database containing 2809 3D DBT volumes acquired from 12 different sites globally is used. DBT is an advanced form of mammography, which uses low-dose X-Rays to image the breast. Different from 2D mammography that superimposes 3D information into one 2D image, DBT creates 3D pictures of the breast tissue and hence allows radiologists to read these pictures and detect breast cancer more easily, especially in dense breast tissues. The xy plane of DBT images has a high spatial resolution of 0.085 mm×0.085 mm which is much larger than the z-dimension of 1 mm. The structures in the z-dimension are not only compressed during the imaging process, but the 3D volumetric information also has large variations due to imaging artifacts.

Experienced radiologists annotate and validate the lesions in DBT volumes, which might contain zero to several lesions. Each lesion is approximately annotated with a 3D bounding box. To train the proposed networks as lesion detection networks, 3D multi-variant Gaussian heat maps may be generated that have the same sizes as the original images as $$f(p) = \sum_{\mu_i, \Sigma_i} \frac{\exp\left(-\frac{1}{2}(p-\mu_i)^T \sum_i (p-\mu_i)\right)}{\sqrt{\det(2\pi \Sigma_i)}} \qquad (5)$$

where p is a 3D coordinate x, y, z; $\mu_i$ is the center coordinate of each lesion 3D bounding box; $\Sigma_i$ is the covariant matrix of the i-th Gaussian determined by the height, width and depth of the 3D bounding box. It should be noted that it is not necessary to directly predict the bounding box coordinates as the general object detection methods such as Faster RCNN because it is sometimes challenging to define the exact boundary of a breast lesion. Also, the voxel-wise confidence maps of lesion presence could be more helpful for clinical decision support than bounding boxes.

The database is randomly split into training and test sets as described in the table below:

|  | #Volumes | #Positives | #Lesions |
| --- | --- | --- | --- |
| Train | 2678 | 1111 | 1375 |
| Test | 131 | 58 | 72 |

More specifically, this table shows the numbers of volumes (#Volumes), lesion-positive volumes (#Positive) and lesions (#Lesions) in the evaluated DBT dataset. A volume or a 3D patch is considered positive if at least one lesion is annotated by the radiologist. For training, 256×256×32 3D patches were extracted. 70% of the training patches were sampled as positives with at least one lesion included, considering the balance between the voxels within and without a breast lesion. The patches were sampled online asynchronously with the network training to form the mini-batches.

Along with the disclosed networks, 2D and 3D U-Nets were trained with the identical architecture and parameters as two base-line comparisons. The 2D U-Net is also trained with input having three input channels. The 3D U-Net is trained with the same patch sampling strategies as the AH-Net. All the networks were trained till convergence then the L2 loss function is replaced with the Focal Loss described in Section 3.4 for hard-voxel mining. The number of convolutional layers and parameters is shown in the table below:

| Network | #Conv Layers | #Parameters |
|---|---|---|
| 2D-UNet | 15 | 28,254,528 |
| 3D-UNet | 15 | 5,298,768 |
| ResNet50 | 53 | 23,507,904 |
| GCN | 94 | 23,576,758 |
| AH-Net | 123 | 27,085,500 |

This table shows number of convolutional layers (#Conv Layers) and model float parameters (#Parameters) respectively in 2D-UNet, 3D-UNet, ResNet50, GCN and AH-Net. ResNet50 is shown here as a reference to be compared with GCN with a simple decoder added.

Using 2D networks, such as the MC-GCN and the 2D U-Net, to process 3D volumes involves repeatedly feeding duplicated images slices. Thus, they could be slower than the 3D networks when they are used for processing 3D volumes. The GPU inference time of four networks was measured by forwarding a 3D DBT volume of size 384×256×64 volume computed by averaging 1000 inferences on an NVIDIA GTX 1080Ti GPU. The time spent on operations such as volume slicing is not included in the timing. The mean GPU time (ms) is shown in the table below:

|  | 2D U-Net | 3D U-Net | MC-GCN | 3D AH-Net |
|---|---|---|---|---|
| Ms | 699.3 | 2.3 | 775.2 | 17.7 |

The GPU inference of AH-Net is 43 times faster than MC-GCN though AH-Net has more parameters. The speed gain could be brought mostly by avoiding repetitive convolutions on the same slices required by multi-channel 2D networks.

Figure 4:
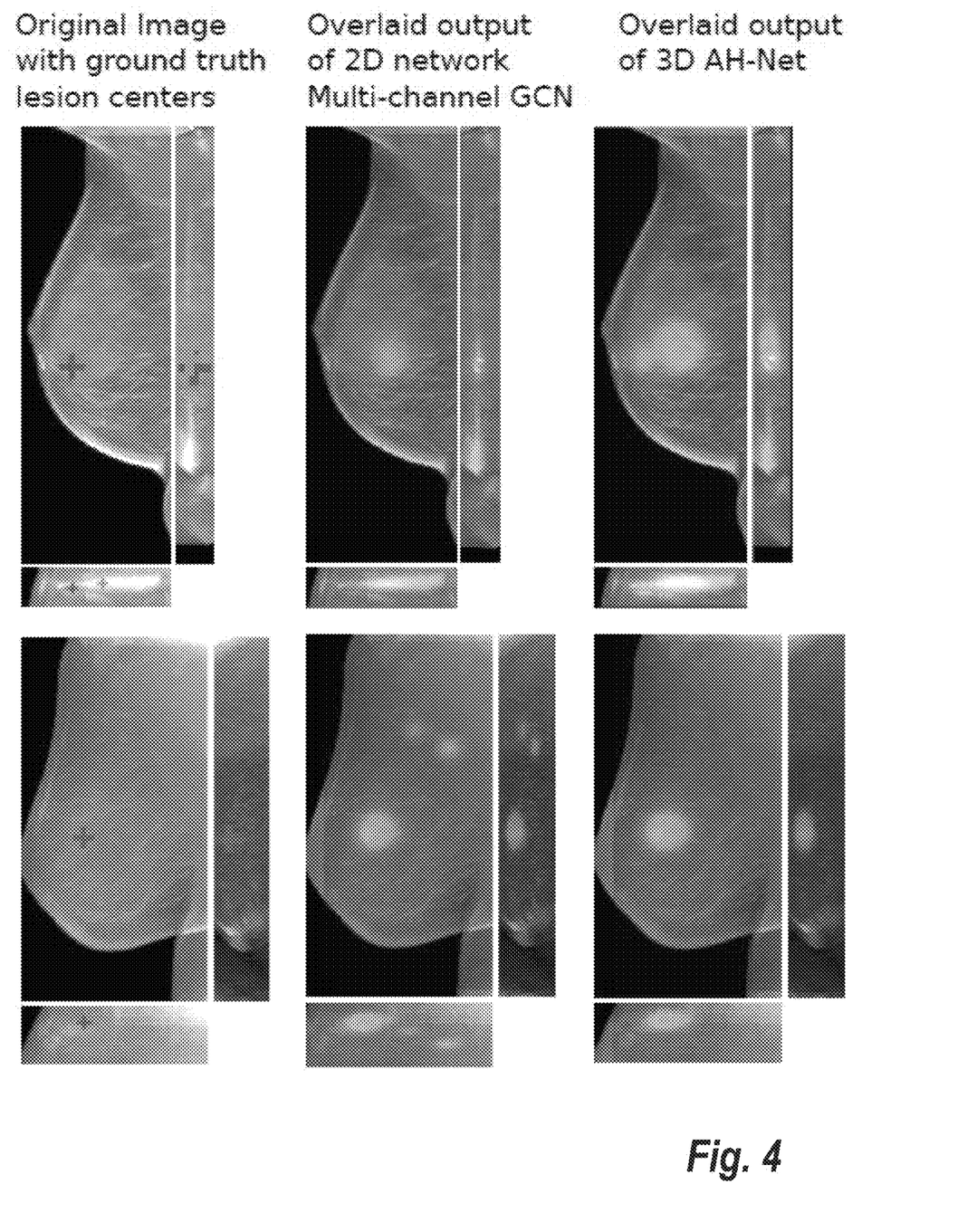
FIG. 4 shows the visual comparisons of the network responses on 2 different DBT volumes from 2D GCN and the 3D AH-Net with the encoder weights transferred from it.

Non-maximal suppression is performed on the network output map to obtain the lesion locations. The network responses at the local maximal voxels are considered as the confidence scores of the cancerous findings. FIG. 4 shows a visual comparison of the networks output. More specifically, this figure shows the visual comparisons of the network responses on 2 different DBT volumes from 2D GCN and the 3D AH-Net with the encoder weights transferred from it. Each volume is visualized with the maximum intensity projection of the xy plane (top-left), the xz plane (bottom) and the yz plane (right). The ground truth lesion centers are shown on the left. With the additional AH-Net Decoders, 3D AH-Net could effectively detect the missing lesion in the first volume (upper row) and remove the false positives in the second volume (lower row).

Figure 5:
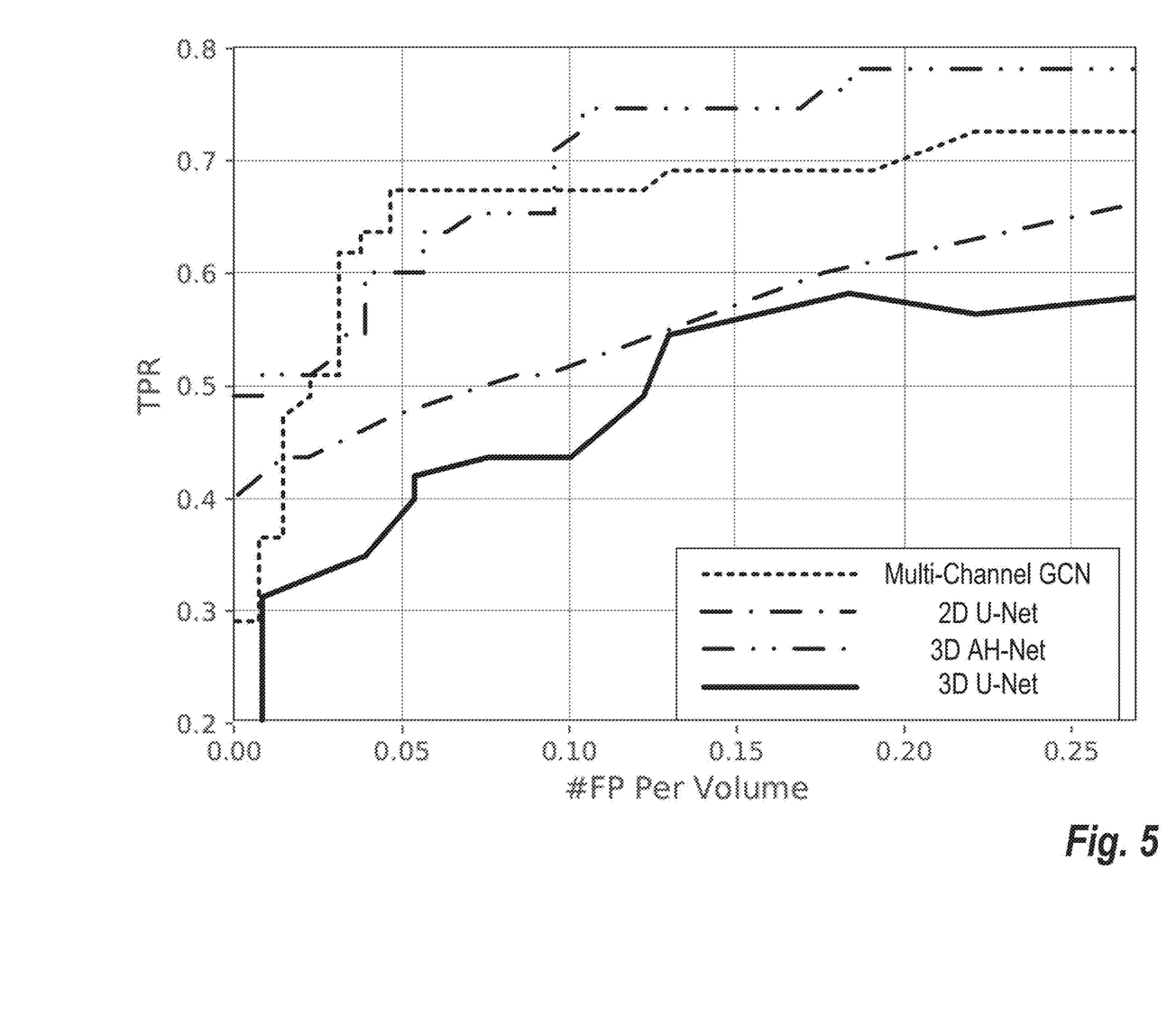
FIG. 5 shows the Free Response Operating Characteristic (FROC) curves regarding the lesion detection performance.

By altering a threshold to filter the response values, the balance between the False Positive Rate (FPR) and True Positive Rate (TPR) can be controlled. The lesion detected by the network is considered a true positive finding if the maximal point resides in a 3D bounding box annotated by the radiologist. Similarly, if a bounding box contains a maximal point, it may be denoted as being detected by the network. The maximal points are otherwise considered as false positive findings. The lesion detection performance was evaluated by plotting the Free Response Operating Characteristic (FROC) curves, which measures the True Positive Rate (TPR) against the number of false positive (#FP) allowed per volume. TPR represents the percentage of lesions that have been successfully detected by the network. FPR represents the percentage of lesions that the network predicted that are false positives. As shown in FIG. 5, the AH-Net out-performs both the 2D and 3D U-Net with large margins. Compared to the performance of the 2D network (Multi-Channel GCN), the 3D AH-Net generates higher TPR for a majority of thresholds, except the region around 0.05 per volume false positives. It is noticeable that AH-Net also obtains nearly 50% TPR even when only 0.01 false positive findings are allowed per volume. Interestingly, the performance of 3D-UNet is slightly worse than that of 2D-UNet, though the DBT volumes have three dimensions. This might be caused by the anisotropic resolution of DBT images and the limited number of parameters constrained by the GPU memory. The FROC numbers are summarized in the table below:

|  | FP = 0.01 | FP = 0.05 | FP = 0.10 | FP = 0.15 | FP = 0.20 | FP = 0.25 |
|---|---|---|---|---|---|---|
| 2D U-Net | 0.4238 | 0.4767 | 0.5181 | 0.5723 | 0.6166 | 0.6506 |
| 3D U-Net | 0.2448 | 0.3877 | 0.4381 | 0.5592 | 0.5738 | 0.5733 |
| GCN | 0.3385 | 0.6727 | 0.6727 | 0.6909 | 0.7018 | 0.7272 |
| AH-Net | 0.4931 | 0.6000 | 0.7272 | 0.7454 | 0.7818 | 0.7818 |

In this table, true positive rate (TPR) sampled at five different numbers of false positive (FP) findings allowed are shown in the first five columns.

Liver and Liver Tumor Segmentation from CT

The second evaluation dataset was obtained from the liver lesion segmentation challenge in MICCAI 2017 (lits-challenge.com), which contains 131 training and 70 testing 3D contrast-enhanced abdominal CT scans. Liver lesion is one of the most common cancer world-wide. It is estimated that 28,920 people will die of liver lesion and 40,710 new cases will be diagnosed in 2017. Automatic segmentation of liver and lesion is challenging due to the heterogeneous and diffusive appearance of both liver and lesions. Also, the number, shape, location of the lesions varies a lot among different volumes. The data and ground-truth masks were provided by various clinical sites around the world. The ground truth masks contain both liver and lesion labels. Most CT scans consist of anisotropic resolution: the between-slice resolution ranges from 0.45 mm to 6.0 mm while the within-slice resolution varies from 0.55 mm to 1.0 mm. All scans cover the abdominal regions but may extend to head and feet. Other than the liver lesion, other diseases may also exist in these data, which further increases the task difficulty.

The MC-GCN was trained with pre-trained ResNet50 as the back-bone network. The input size of stacked 2D slices is 512×512 with three channels. After convergence, the weights of the encoder part of MC-GCN were transformed to the corresponding layers of a 3D AH-Net, which is then fine-tuned using 3D patches with size 192×192×64. The weights of other layers were randomly initialized. In the training of both networks, the cross-entropy loss is used at the beginning until convergence, which is then replaced by the Focal Loss for hard voxel mining.

The performance of AH-Net is listed in the table below, together with other six top-ranked submissions retrieved from the LITS challenge leaderboard:

| | Lesion | | Liver | |
|---|---|---|---|---|
| Method | DG | DPC | DG | DPC |
| leHealth | 0.794 | 0.702 | 0.964 | 0.961 |
| H-DenseNet | 0.829 | 0.686 | 0.965 | 0.961 |
| hans.meine | 0.796 | 0.676 | 0.963 | 0.960 |
| medical | 0.783 | 0.661 | 0.951 | 0.951 |
| deepX | 0.820 | 0.657 | 0.967 | 0.963 |
| superAI | 0.814 | 0.674 | — | — |
| GCN | 0.788 | 0.593 | 0.963 | 0.951 |
| 3D AH-Net | 0.834 | 0.634 | 0.970 | 0.963 |

These submissions employ various types of neural network architectures: 2D, 3D,2D-3D hybrid, and model fusion. Two evaluation metrics were adapted: (1) Dice Global (DG) which is the dice score combining all the volumes into one; (2) Dice per Case (DPC) which averages of the dice scores of every single case. The Dice score between two masks is defined as $DICE(A, B)=2|A \cap B|/(|A|+|B|)$. The results achieve the state-of-the-art performance in three of the four metrics, including the dice global score of the lesions, dice global and dice per case score of the livers, which proves the effectiveness of AH-Net for segmenting 3D images with diverse anisotropic resolution.

Figure 6A:
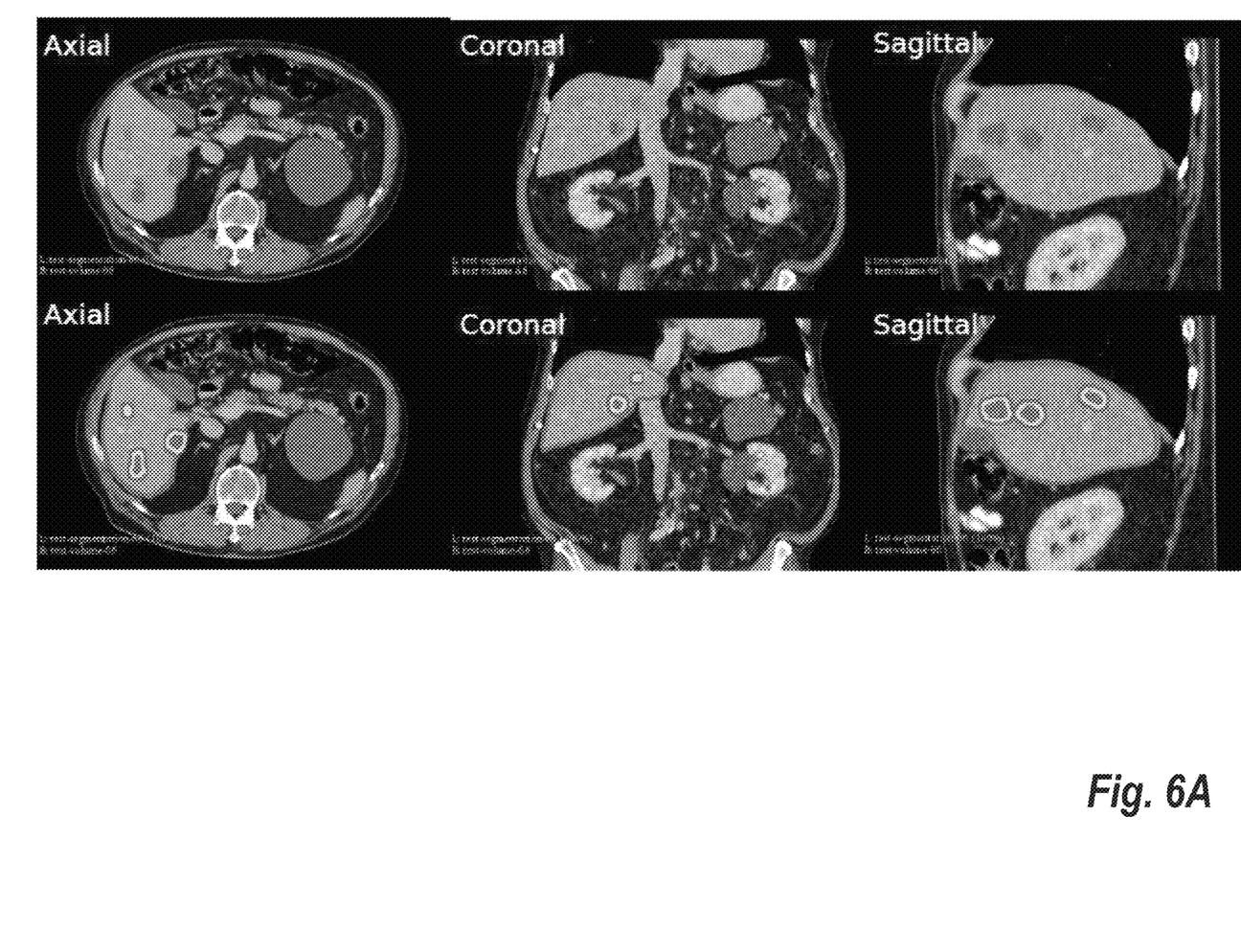
FIG. 6A shows example liver lesion segmentation results from 3D AH-Net.
Figure 6B:
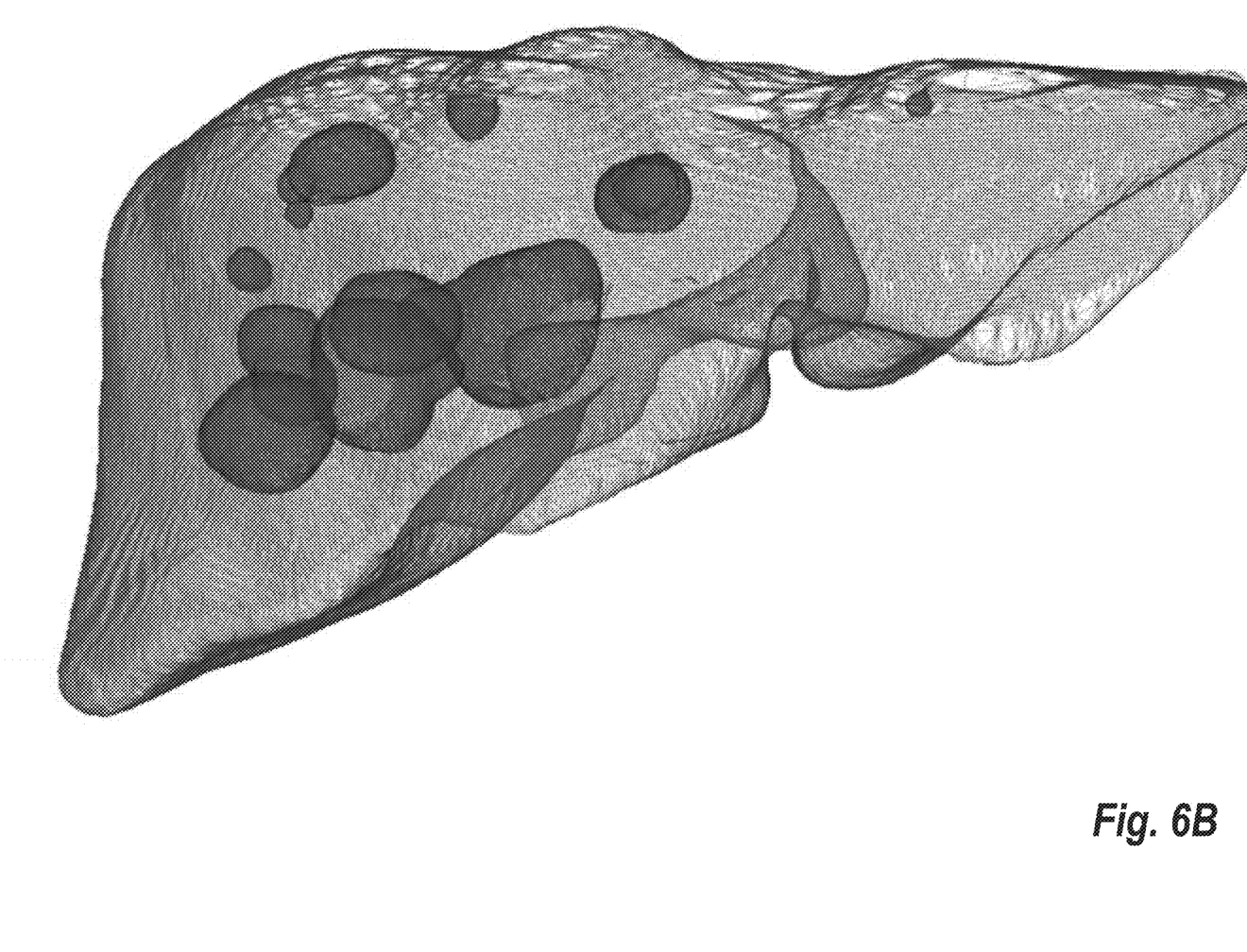
FIG. 6B shows example renderings of the segmentations presented in FIG. 6A.

FIG. 6A shows example liver lesion segmentation results from 3D AH-Net. The segmented contours of liver (blue) and liver lesion (pink) were overlaid on 3 slices viewed from different orientations (Axial, Coronal and Sagittal). The segmentations are rendered in 3D in FIG. 6B.

As a summary of the technique described above, FIG. 7 is an example computer-implemented method 700 for identifying features in 3D image volumes, according to some embodiments of the present invention. Starting at step 705, a 3D volume is divided into a plurality of 2D slices. Techniques for dividing a volume into slices are generally known in the art and, thus, these techniques are not described in detail herein. The thickness of each slice may be selected based on, for example, the fidelity of the image data and the computational resources available for processing.

Figure 7:
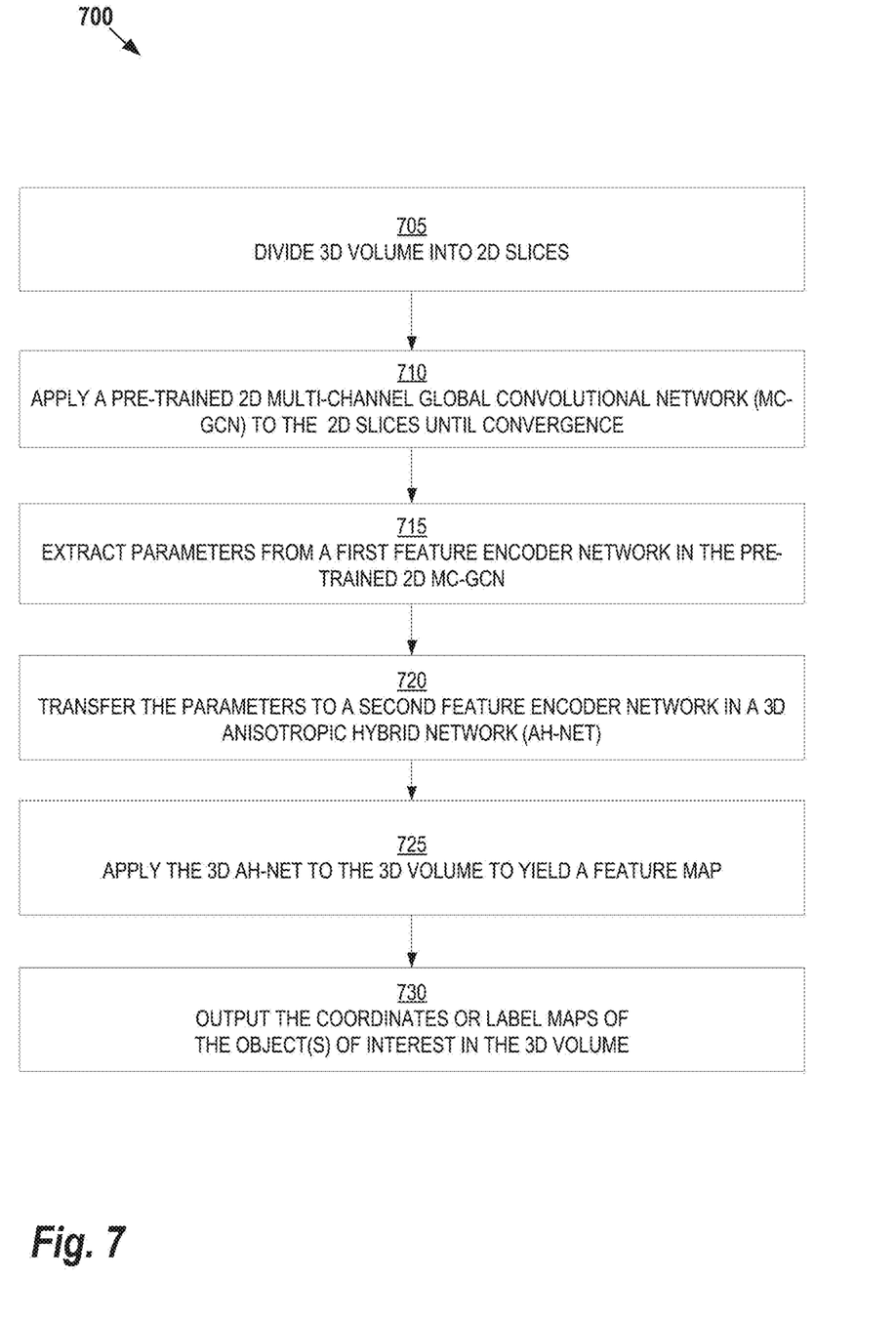
FIG. 7 illustrates an example computer-implemented method for identifying features in 3D image volumes, according to some embodiments of the present invention.

Continuing with reference to FIG. 7, at step 710, a 2D MC-GCN is applied to the 2D slices until convergence. As is generally understood in the art, a neural network such as the 2D MC-GCN "converges" by adjusting the parameters of the neural network (e.g., weights of the nodes) until the error between the desired and actual output is minimized. Thus, at step 710, the 2D MC-GCN is executed on the 2D slices iteratively until the error is minimized. As described above with reference to FIG. 1, the 2D MC-GCN may comprise a multi-layer residual network in some embodiments and may include components such as global convolutional network blocks and boundary refinement blocks. Following convergence of the 2D MC-GCN, the parameters are extracted at step 715 from a first feature encoder network in the 2D MC-GCN.

Next, at step 720, the extracted parameters are transferred to a second feature encoder network in a 3D AH-Net. The method of transfer can vary, depending on how the system is integrated. For example, in embodiments, where the 3D AH-Net and the 2D MC-GCN are executed in a single executable file, the parameters may be "transferred" by simply passing the memory references from the 3D AH-Net to the 2D MC-GCN. Where the 3D AH-Net and the 2D MC-GCN are executed in separate executables files, the parameters may be transferred by copying the parameters from one file to the other or by having the 3D AH-Net read and interpret one or more output files generated by the 2D MC-GCN. Note that this latter implementation would also allow the 3D AH-Net and the 2D MC-GCN to be executed on different computing systems connected via the Internet or another network.

The 3D AH-Net is applied to the 3D volume at step 725 to yield a probability map. As described above with reference to FIG. 2 following application of the feature encoder network, the 3D AH-Net executes a decoder network comprising anisotropic convolutional blocks. Each anisotropic convolutional block applies a plurality of 3D kernels to an output of the second feature encoder network. Briefly, the 3D AH-Net calculates a summation of the output of anisotropic convolutional blocks and applies a pyramid volumetric pooling operation to the summation of the output anisotropic convolutional blocks to yield a probability map pyramid. Then, the summation of the output of plurality of anisotropic convolutional blocks is concatenated with the probability map pyramid to yield the probability map.

Returning to FIG. 7, at step 730, using the probability map, one or more of (a) coordinates of the objects with non-maximum suppression or (b) a label map of objects of interest in the 3D volume are generated. As noted above, the output of AH-Net is the probability map. In embodiments such as depicted in FIG. 7, post-processing techniques generally known in the art may be performed on the probability map to get either the coordinates of the objects with non-maximum suppression or the label map of the objects by thresholding the probability map. In other embodiments, the probability map may be used to derive a voxel-wise confidence map of lesion presence comprising a confidence score for each voxel in the 3D volume indicating presence or absence of a lesion. In some embodiments, the probability map is presented overlaid on the 3D volume. For example, in one embodiment, the probability map is presented as a heat map overlaid on the 3D volume.

Figure 8:
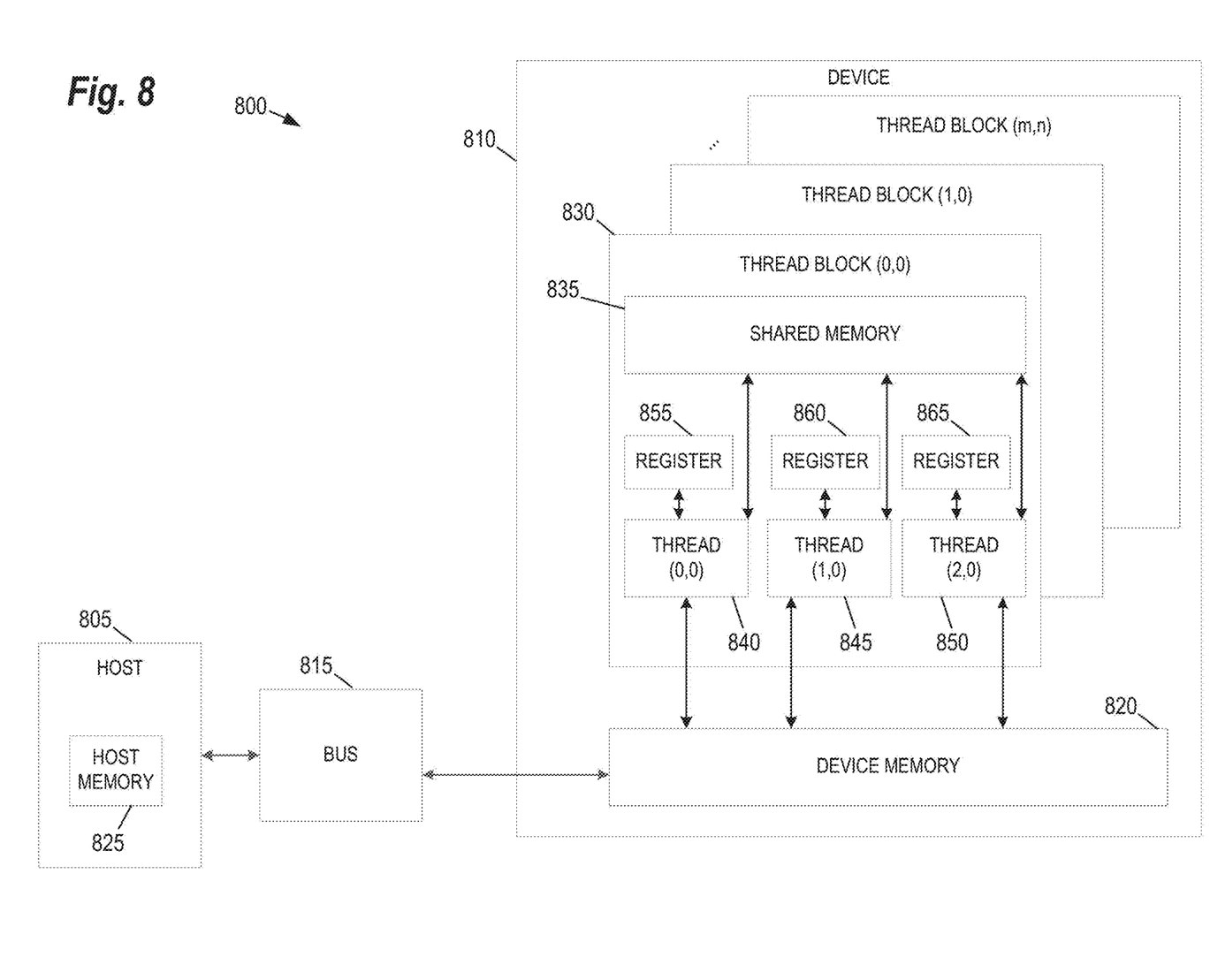
FIG. 8 provides an example of a parallel processing memory architecture that may be utilized by to perform computations related to execution of the algorithms discussed herein, according to some embodiments of the present invention.

FIG. 8 provides an example of a parallel processing memory architecture 800 that may be utilized to perform computations related to execution of the algorithms discussed herein, according to some embodiments of the present invention. This architecture 800 may be used in embodiments of the present invention where NVIDIA™ CUDA (or a similar parallel computing platform) is used. The architecture includes a host computing unit ("host") 805 and a GPU device ("device") 810 connected via a bus 815 (e.g., a PCIe bus). The host 805 includes the central processing unit, or "CPU" (not shown in FIG. 8) and host memory 825 accessible to the CPU. The device 810 includes the graphics processing unit (GPU) and its associated memory 820, referred to herein as device memory. The device memory 820 may include various types of memory, each optimized for different memory usages. For example, in some embodiments, the device memory includes global memory, constant memory, and texture memory.

Parallel portions of a deep learning application may be executed on the architecture 800 as "device kernels" or simply "kernels." A kernel comprises parameterized code configured to perform a particular function. The parallel computing platform is configured to execute these kernels in an optimal manner across the architecture 800 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below).

Using concurrent kernel execution, streams, and synchronization with lightweight events, the architecture 800 of FIG. 8 (or similar architectures) may be used to parallelize training of a deep neural network. For example, in some embodiments, the individual layers of the encoder in the 3D AH-Net may be executed in parallel on the imaging data. Similarly, the 3D AH-Net's decoder modules, may be implemented such that various operations are done in parallel.

The device 810 includes one or more thread blocks 830 which represent the computation unit of the device 810. The term thread block refers to a group of threads that can cooperate via shared memory and synchronize their execution to coordinate memory accesses. For example, in FIG. 8, threads 840, 845 and 850 operate in thread block 830 and access shared memory 835. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 8, the thread blocks 830 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. In some embodiments, processing of subsets of the training data or operations performed by the algorithms discussed herein may be partitioned over thread blocks automatically by the parallel computing platform software. However, in other embodiments, the individual thread blocks can be selected and configured to optimize training of the deep neural network. For example, in one embodiment, each thread block is assigned a subset of training data with neighboring or overlapping values.

Continuing with reference to FIG. 8, registers 855, 860, and 865 represent the fast memory available to thread block 830. Each register is only accessible by a single thread. Thus, for example, register 855 may only be accessed by thread 840. Conversely, shared memory is allocated per thread block, so all threads in the block have access to the same shared memory. Thus, shared memory 835 is designed to be accessed, in parallel, by each thread 840, 845, and 850 in thread block 830. Threads can access data in shared memory 835 loaded from device memory 820 by other threads within the same thread block (e.g., thread block 830). The device memory 820 is accessed by all blocks of the grid and may be implemented using, for example, Dynamic Random-Access Memory (DRAM).

Each thread can have one or more levels of memory access. For example, in the architecture 800 of FIG. 8, each thread may have three levels of memory access. First, each thread 840, 845, 850, can read and write to its corresponding registers 855, 860, and 865. Registers provide the fastest memory access to threads because there are no synchronization issues and the register is generally located close to a multiprocessor executing the thread. Second, each thread 840, 845, 850 in thread block 830, may read and write data to the shared memory 835 corresponding to that block 830. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 810 to read and/or write to the device memory. Device memory requires the longest time to access because access must be synchronized across the thread blocks operating on the device. Thus, in some embodiments, the processing of each seed point is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 8, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

As used herein, the term "module" can refer to either or both of: (i) a software component that causes an electronic device to accept various inputs and generate certain outputs; or (ii) an electronic input/output interface, such as a panel, frame, textbox, window or other portion of a GUI.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

We claim:

1. A computer-implemented method for identifying features in 3D image volumes, the method comprising:
dividing a 3D volume into a plurality of 2D slices;
applying a pre-trained 2D multi-channel global convolutional network (MC-GCN) to the plurality of 2D slices until convergence;
following convergence of the 2D MC-GCN, extracting a plurality of parameters from a first feature encoder network in the 2D MC-GCN;
transferring the plurality of parameters to a second feature encoder network in a 3D Anisotropic Hybrid Network (AH-Net);
applying the 3D AH-Net to the 3D volume to yield a probability map; and
using the probability map, generate one or more of (a) coordinates of the objects with non-maximum suppression or (b) a label map of objects of interest in the 3D volume.

2. The method of claim 1, wherein the 2D MC-GCN comprises a multi-layer residual network.

3. The method of claim 2, wherein the 2D network further comprises a plurality of global convolutional network blocks and a plurality of boundary refinement blocks.

4. The method of claim 2, wherein following application of the second feature encoder network, the 3D AH-Net executes a decoder network comprising a plurality of anisotropic convolutional blocks.

5. The method of claim 4, wherein each anisotropic convolutional block applies a plurality of 3D kernels to an output of the second feature encoder network.

6. The method of claim 4, wherein applying the 3D AH-Net to the 3D volume to yield the probability map comprises:
calculating a summation of the output of plurality of anisotropic convolutional blocks;
applying a pyramid volumetric pooling operation to the summation of the output of plurality of anisotropic convolutional blocks to yield a probability map pyramid;
concatenating the summation of the output of plurality of anisotropic convolutional blocks with the probability map pyramid to yield the probability map.

7. The method of claim 1, wherein the label map is presented as a heat map overlaid on the 3D volume.

8. A computer-implemented method for identifying features in 3D image volumes, the method comprising:
dividing a 3D digital breast tomosynthesis (DBT) volume into a plurality of 2D slices;
applying a 2D multi-channel global convolutional network (MC-GCN) to the plurality of 2D slices until convergence, wherein the 2D MC-GCN is pre-trained with a plurality of DBT image slices depicting healthy breast tissue;
following convergence of the 2D MC-GCN, extracting a plurality of parameters from a first feature encoder network in the 2D MC-GCN;
transferring to the plurality of parameters to a second feature encoder network in a 3D Anisotropic Hybrid Network (AH-Net);
applying the 3D AH-Net to the 3D volume to yield a voxel-wise confidence map of lesion presence comprising a confidence score for each voxel in the 3D volume indicating presence or absence of a lesion; and
presenting the voxel-wise confidence map overlaid on the 3D DBT volume.

9. The method of claim 8, wherein the 2D MC-GCN comprises a multi-layer residual network.

10. The method of claim 9, wherein the 2D MC-GCN further comprises a plurality of global convolutional network blocks and a plurality of boundary refinement blocks.

11. The method of claim 9, wherein following application of the second feature encoder network, the 3D AH-Net executes a decoder network comprising a plurality of anisotropic convolutional blocks.

12. The method of claim 11, wherein each anisotropic convolutional block applies a plurality of 3D kernels to an output of the second feature encoder network.

13. The method of claim 11, wherein applying the 3D AH-Net to the 3D volume to yield the probability map comprises:
calculating a summation of the output of plurality of anisotropic convolutional blocks;
applying a pyramid volumetric pooling operation to the summation of the output of plurality of anisotropic convolutional blocks to yield a probability map pyramid;
concatenating the summation of the output of plurality of anisotropic convolutional blocks with the probability map pyramid to yield the probability map.

14. A system for identifying features in 3D image volumes, the system comprising:
a multi-channel 2D global convolutional neural network (MC-GCN) comprising a 2D feature encoder network;
a 3D Anisotropic Hybrid Network (AH-Net) comprising:
a 3D feature encoder network,
a plurality of decoder modules configured to process outputs of the 3D feature encoder,
a pyramid volumetric pooling module configured to process outputs of the plurality of decoder modules to generate a probability map pyramid, and
a concatenation module configured to concatenate the probability map pyramid and outputs of the plurality of decoder modules to generate a probability map;
a parallel processing architecture configured to:
divide a 3D volume into a plurality of 2D slices;
apply the 2D MC-GCN to the plurality of 2D slices until convergence;
following convergence of the 2D MC-GCN, extract a plurality of parameters from a 2D feature encoder network in the 2D MC-GCN;
transferring to the plurality of parameters to the 3D feature encoder network in the 3D AH-Net; and applying the 3D AH-Net to the 3D volume to generate a probability map.

15. The system of claim 14, further comprising:
a display configured to present a label map of objects of interest in the 3D volume derived from the probability map overlaid on the 3D volume.

16. The system of claim 14, wherein the 3D feature encoder network is a multi-layer residual network.

17. The system of claim 14, wherein the outputs of each decoder module are combined via summation prior to processing by the pyramid volumetric pooling module.

* * * * *